United States Patent [19]

Nakamura et al.

[11] Patent Number: 5,144,346
[45] Date of Patent: Sep. 1, 1992

[54] OPHTHALOMOLOGICAL APPARATUS FOR ALIGNMENT AND REFRACTION

[75] Inventors: Yukitsugu Nakamura, Sagamihara; Yoshimi Kohayakawa, Yokohama; Hiroshi Aoki, Kawasaki, all of Japan

[73] Assignee: Canon Kabushiki Kaisha, Tokyo, Japan

[21] Appl. No.: 691,782

[22] Filed: Apr. 26, 1991

[30] Foreign Application Priority Data

| Apr. 27, 1990 | [JP] | Japan | 2-112909 |
| May 18, 1990 | [JP] | Japan | 2-128388 |
| Jun. 1, 1990 | [JP] | Japan | 2-143457 |
| Jun. 15, 1990 | [JP] | Japan | 2-156969 |

[51] Int. Cl.$^5$ .............................. A61B 3/14
[52] U.S. Cl. ............................. 351/208; 351/211
[58] Field of Search ............ 351/208, 211, 214, 221; 128/633, 745

[56] References Cited

U.S. PATENT DOCUMENTS 3,832,066  8/1974  Cornsweet .
4,275,964  6/1981  Vassiliadis .
4,609,287  9/1986  Kohayakawa .
4,697,895  10/1987  Sekiguchi et al. .
4,761,070  8/1988  Fukuma .
4,820,037  4/1989  Kohayakawa et al. .
4,826,315  5/1989  Kohayakawa .

FOREIGN PATENT DOCUMENTS 63-53433  3/1988  Japan .

Primary Examiner—Rodney B. Bovernick
Attorney, Agent, or Firm—Fitzpatrick, Cella, Harper and Scinto

[57] ABSTRACT

An ophthalmological apparatus is arranged in such a manner that different measuring light sources are provided for an eye refractive power measuring system and a lens refractive power measuring system. A light sensor of the lens refractive power measuring system is commonly used as at least either the light sensor for an alignment observing system or the light sensor for the eye refractive power measuring system. A lens to be examined can be placed at a position which is different from a position where an eye to be examined is placed.

12 Claims, 10 Drawing Sheets ated
OPHTHALOMOLOGICAL APPARATUS FOR ALIGNMENT AND REFRACTION

BACKGROUND OF THE INVENTION

1. Field of the Invention

The present invention relates to an ophthalomological apparatus for use e.g. in ophthalmic hospitals and capable of measuring the refractivity of the eye to be examined, a lens of glasses and a contact lens.

2. Related Background Art

Hitherto, the refractivity of the eye to be examined has been objectively measured by using, for example, an auto-refractometer. In a case where the person to be examined has glasses or contact lenses, the refractivity at the vertex of the lens is also measured by using a lens meter so that whether or not the lens is suitable for the eye to be examined is determined.

However, the above-described conventional technology encounters problems in that the overall cost cannot be reduced, a large space is necessary to perform the measurement operation, and it takes long time to complete the measurement, because individual apparatuses are required to measure the refractivity of the eye to be examined and that of the lens to be fitted to the eye to be examined. In order to overcome the above-described problems, there has been disclosed an ophthalmological apparatus in Japanese Patent Application Laid-Open No. 63-53433 which is arranged in such a manner that a lens to be examined is, as an alternative to the eye to be examined, placed at the position at which the eye to be examined is placed, whereby the refractivity of the eye to be examined and that of the lens to be examined can be alternately measured.

SUMMARY OF THE INVENTION

An object of the present invention is to provide an improved ophthalmological apparatus capable of quickly measuring the refractivity of the eye to be examined and that of a lens of glasses for the eye to be examined.

Another object of the present invention is to provide an ophthalmological apparatus with which an examiner can easily perform the alignment operation before the refractivity of the eye to be examined and that of the lens to be examined are measured.

Other and further objects, features and advangates of the invention will be appear more fully from the following description.

DETAILED DESCRIPTION OF THE PREFERRED EMBODIMENTS

Preferred embodiments of the present invention will now be described with reference to the drawings.

Figure 1:
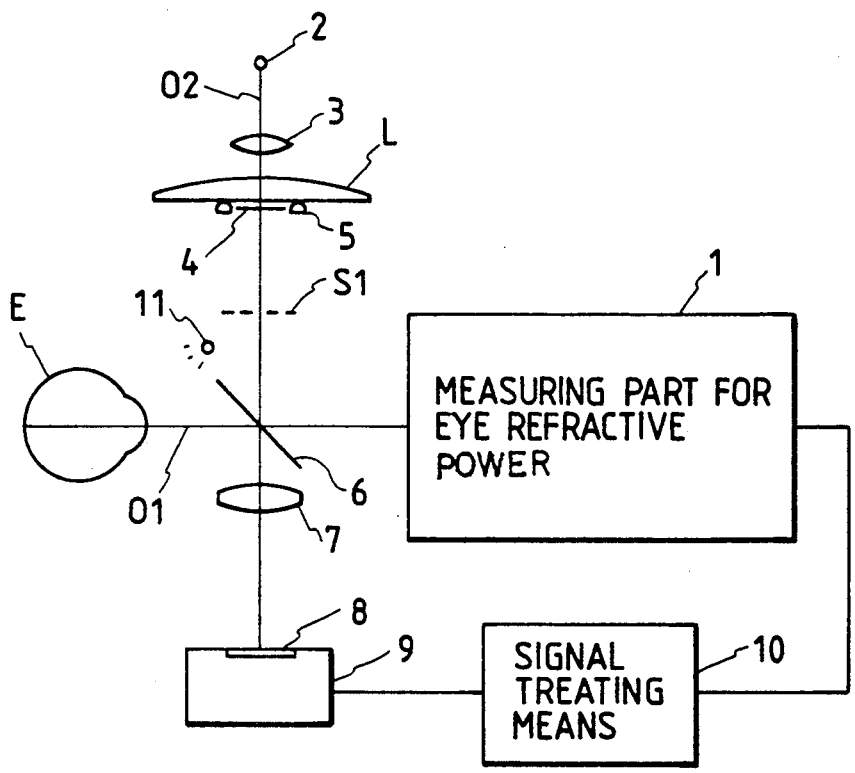
FIG. 1 is a schematic view which illustrates a first embodiment of the present invention.
Figure 2:
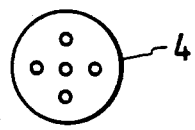
FIGS. 2 and 5 are front elevational views which illustrate diaphragms.

FIG. 1 is a structural view which illustrates a first embodiment of the present invention. Referring to FIG. 1, the eye refractive power of eye E to be examined is measured by a measuring part 1 for eye refractive power which includes a light source and an light sensor for measuring the eye refractive power. The measuring part 1 is disposed opposite eye E to be examined on an optical axis 01 which substantially coincides with the visual line of eye E to be examined. On the other hand, a measuring light source 2 is disposed on an optical axis 02, which is perpendicular to the optical axis 01 at a position between the eye E to be examined and the measuring part 1 for the eye refractive power, the measuring light source 2 acting to measure the refractive power of a lens L to be examined. When viewed from the measuring light source 2 portion, there are successively disposed a lens 3, a diaphragm 4, a holding member 5 for holding the lens L to be examined, a dichroic mirror 6, which is arranged to reflect light in a direction which is made coincide with the optical axis 01, a lens 7 and an imaging element 8. The output from the imaging element 8 is connected to an imaging means 9. The output from the measuring part 1 for the eye refractive power and that of the imaging means 9 are respectively connected to a signal treating means 10. An illuminating light source 11 is disposed in front of the eye E to be examined so that the eye E to be examined is irradiated with illuminating light.

The holding member 5 is disposed away from a position S1 which is conjugate with the imaging element 8 positioned on the optical axis 02. The imaging element 8 and the lens L to be examined are positioned while having a non-conjugated positional relationship. The dichroic mirror 6 has spectral characteristics of transmitting and reflecting, that is, a beam emitted from a light source (omitted from illustration) disposed in the measuring part 1 for the eye refractive power and that emitted from the measuring light source 2 are transmitted though the dichroic mirror 6. Furthermore, a beam emitted from the illuminating light source 11 is reflected at the dichroic mirror 6. The imaging element 8 has a characteristic of sensing the beams emitted from the measuring light source 2 and the illuminating light source 11.

When the refractive power of the eye E to be examined is measured, the illuminating light source 11 is first turned on for the purpose of observing the alignment. The beam emitted from the illuminating light source 11 is projected to the anterior eye portion of the eye E to be examined. The light reflected at the anterior eye portion of the eye E to be examined travels along the optical axis 01, and is reflected by the dichroic mirror 6. As a result, it is, via the lens 7, imaged on the imaging element 8 which is conjugate with the anterior eye portion, as the image of the anterior eye portion. The thus obtained image of the anterior eye portion is converted into a video signal by the imaging means 9 to signal treating means 10 so as to be transmitted and displayed on a TV monitor or the like (omitted from illustration), whereby the operator is able to perform the alignment of the eye E to be examined while observing the picture displayed on the monitor. It is apparent for those skilled in the art that observations of the image of the anterior eye and/or the image of the cornea formed by reflecting a beam emitted from an alignment index light source are utilized for the purpose of the alignment.

Then, the illuminating light source 11 is turned off and the light source (omitted from illustration) disposed in the measuring part 1 for the eye refractive power is turned on. As a result, the beam emitted from the above-described light source travels along the optical axis 01 to reach to the eye E to be examined. The beam reflected at the eye fundus of the eye E to be examined returns along the same optical path so as to be received by the imaging element or the like serving as the light sensor, which is included in the measuring part 1 for the eye refractive power Information about the receiving position is, similar to a video signal, transmitted to the signal treating means 10 in which the refractive power of the eye E to be examined is calculated.

Figure 3:
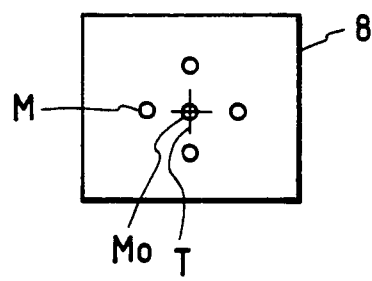
FIGS. 3, 4 and 6 illustrate projected beam images formed on an imaging element.

When the refractive power of the lens L to be examined is measured, the measuring light source 2 is turned on while bringing the lens L to be examined into contact with the holding member 5. The beam emitted from the measuring light source 2 is made to be a collimated beam by the lens 3. The collimated beam is then incident upon the lens L to be examined, and is transmitted and refracted. Then, the transmitted and refracted beam passes through the dichroic mirror 6 via the diaphragm 4 so that five refracted beams M are projected to the surface of the imaging element 8 as shown in FIG. 3. The information about the positions of the beams M are converted into video signals by the imaging means 9 and is transmitted to the signal treating means 10. Since the relative position between the above-described beams M is changed depending upon the value of the refractive power of the lens L to be examined, the refractive power of the lens L to be examined can be calculated in the measuring part 1 for the eye refractive power from said positional relationship.

Figure 4:
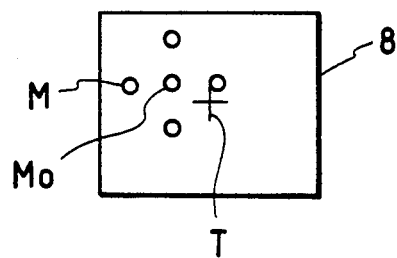

In a state that the lens L to be examined is deviated from the optical axis 02, all of the five beams M have moved on the imaging element 8 as shown, for example, in FIG. 4. Therefore, for example, the lens L to be examined can easily be aligned by an examiner in such a manner that a mark T is previously electrically generated at the position of the optical axis 02 on the imaging element 8 and a central beam M0 is, by the examiner, aligned with the mark T while observing the imaging element 8.

Figure 5:
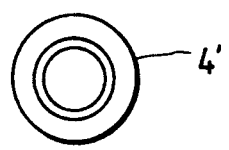
Figure 6:
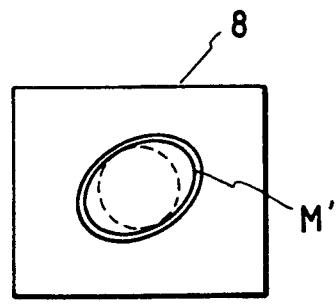

At least three apertures must be formed in the diaphragm 4 in addition to the central aperture for establishing the alignment with the mark T, so that the refractive power can be calculated. The diaphragm 4 may be replaced by a diaphragm 4' having, as shown in FIG. 5, an annular aperture. In this case, beam M' as shown in FIG. 6 is formed on the imaging element 8. The shape of the thus formed annular beam M' is used to calculate the refractive power, and the alignment is performed in such a manner that the center of the beam M' is aligned with the optical axis 02.

Figure 7:
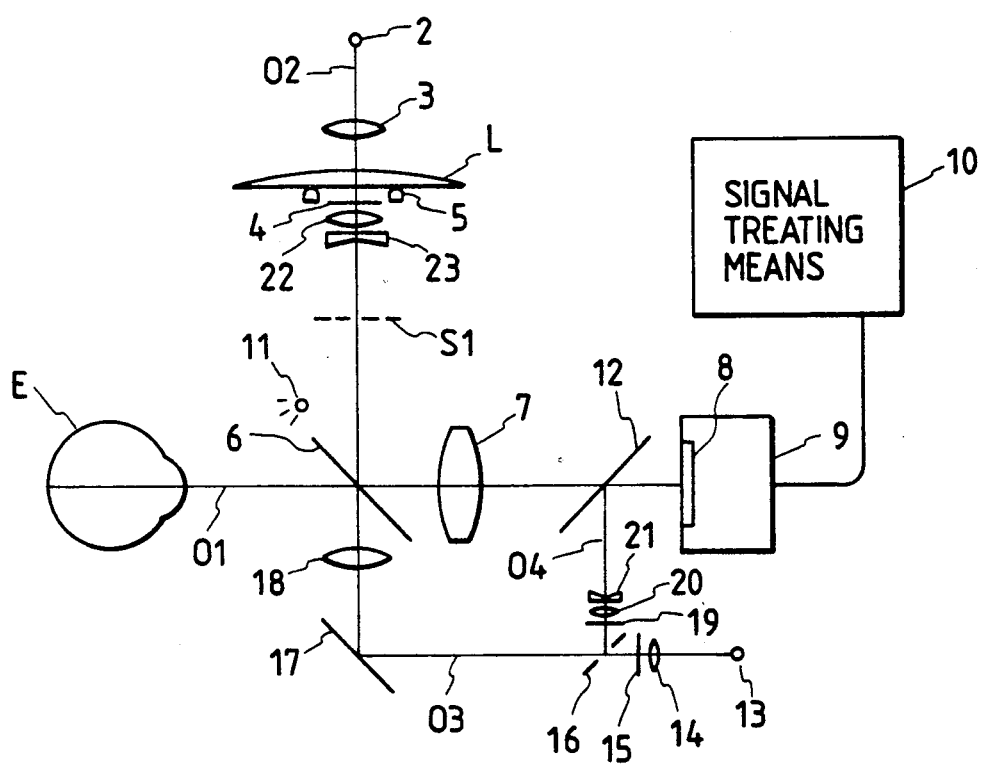
FIG. 7 is a schematic view which illustrates a second embodiment of the present invention.
Figure 8:
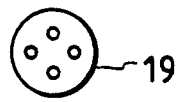
FIG. 8 is a front elevational view which illustrates the diaphragm.
Figure 9:
FIG. 9 is a front elevational view which illustrates a separation prism.

FIG. 7 is a structural view which illustrates a second embodiment of the apparatus according to the present invention, where the same reference numerals as those shown in the above-described embodiment represent the same elements. When viewed from the portion in the vicinity of the eye E to be examined, there are successively disposed the dichroic mirror 6, the lens 7, a dichroic mirror 12 and the imaging element 8 on the optical axis 01 which substantially coincides with a glance of the eye E to be examined. The output from the imaging element 8 is connected to the imaging means 9, while the output from the imaging means 9 is connected to the signal treating means 10. In order to measure the refractive power of the eye E to be examined, a measuring light source 13 is provided. On an optical axis 03 established from the measuring light source 13 to the eye E to be examined, a lens 14, a central aperture 15, a mirror 16 having an aperture, a mirror 17 arranged to reflect light into a direction which is made to coincide with the optical axis. Furthermore, a lens 18 is disposed on the optical axis 02. On an optical axis 04 established in the direction into which the mirror 16 having an aperture reflects light, there are disposed a 4-aperture diaphragm 19 having, as shown in FIG. 8, four apertures, a lens 20 and a separation prism 21 composed of four wedge prisms as shown in FIG. 9. A lens 22 and another separation prism 23 having the same structure as that of the separation prism 21 are, in this sequential order, disposed on the optical axis 02 established between a group of elements disposed on the optical axis 02 and the dichroic mirror 6, the group being consisting of the measuring light source 2, the lens 3, the diaphragm 4 and the holding member 5. The dichroic mirror 6 has spectrum characteristics with which it reflects infrared rays emitted from the measuring light sources 2 and 13 and transmits a beam emitted from the illuminating light source 11. On the other hand, the dichroic mirror 12 has spectrum characteristics with which it transmits a beam emitted from the illuminating light source 11 and reflects the infrared ray emitted from the measuring light source 13.

When the refractive power of the eye E to be examined is measured with the apparatus thus structured, the illuminating light source 11 is first turned on so that the eye E to be examined is radiated by the beam emitted from the illuminating light source 11. The beam reflected at the anterior eye portion passes through the dichroic mirror 6 and through the lens 7 and the dichroic mirror 12, and then the image of the anterior eye portion is formed on the imaging element 8.

When the refractive power of the eye E to be examined is measured, the illuminating light source 11 is turned off but the measuring light source 13 is turned on. The beam emitted from the measuring light source 13 passes along the optical axis 03 in such a manner that it passes through the lens 14, the central aperture diaphragm 15 and the mirror 16 having an aperture before it is reflected by the mirror 17. Then, it passes through the lens 18 before it is reflected by the dichroic mirror 6. As a result, it reaches to the eye E to be examined. The beam reflected at the eye fundus of the eye E to be examined returns along the same optical path in such a manner that it is reflected by the mirror 16 having an aperture before it passes through the 4-aperture diaphragm 19 and the lens 20. Then, it is separated from the optical axis 04 by the separation prism 21 before it is reflected by the dichroic mirror 12. Then, the four beams are imaged on the imaging element 8 so that the positions of the beams are, similar to the first embodiment, imaged by the imaging means 9. Consequently, the refractive power of the eye E to be examined is calculated in the signal treating means 10.

On the other hand, when the refractive power of the lens L to be examined is measured, and the measuring light source 2 is turned on. The beam emitted from the measuring light source 2 passes through the lens 3 before it is refracted by the lens L to be examined. Then, it passes through the diaphragm 4 and the lens 22 before it is separated from the optical axis 02 by the separation prism 23. Subsequently, it is reflected by the dichroic mirror 6 before it passes through the lens 7 and the dichroic mirror 12. As a result, the four beams are imaged on the imaging element 8 so that the refractive power is, similar to the above-described cases, calculated from the positioned relationship between the four beams.

According to this embodiment, the imaging element 8 for observing the anterior eye portion of the eye E to be examined is also used to measure the refractive power of the lens L to be examined. Furthermore, the imaging element 8 and the lens L to be examined have a non-conjugated relationship. If the structure is arranged in such a manner that the beam refracted by the lens L to be examined is introduced into the four-aperture diaphragm 19, the lens 20 and the separation prism 21 for use to measure the refractive power of the eye E to be examined, the diaphragm 4, the lens 22 and the separation prism 23 can be omitted from the structure.

As described above, the refractometer according to this embodiment is arranged in such a manner that the holding member for holding the lens to be examined is disposed at the non-conjugated position with respect to the position of the imaging means for imaging the anterior eye portion of the eye to be examined. The beam is projected to the lens to be examined which has been hold as described above. The beam refracted by the lens to be examined is introduced into the imaging means so that the refractive power is measured from the refracted beams formed on the imaging means. Accordingly, the imaging means for observing the anterior eye portion of the eye to be examined is also used to measure the refractive power, so that the structure of the refractometer can be simplified. Furthermore, the lens to be examined can easily be aligned by the examiner since the examiner observes the positions of the refracted beams formed on the imaging means. Therefore, an excellent operation facility is realized if it is used as a lens meter.

Figure 10:
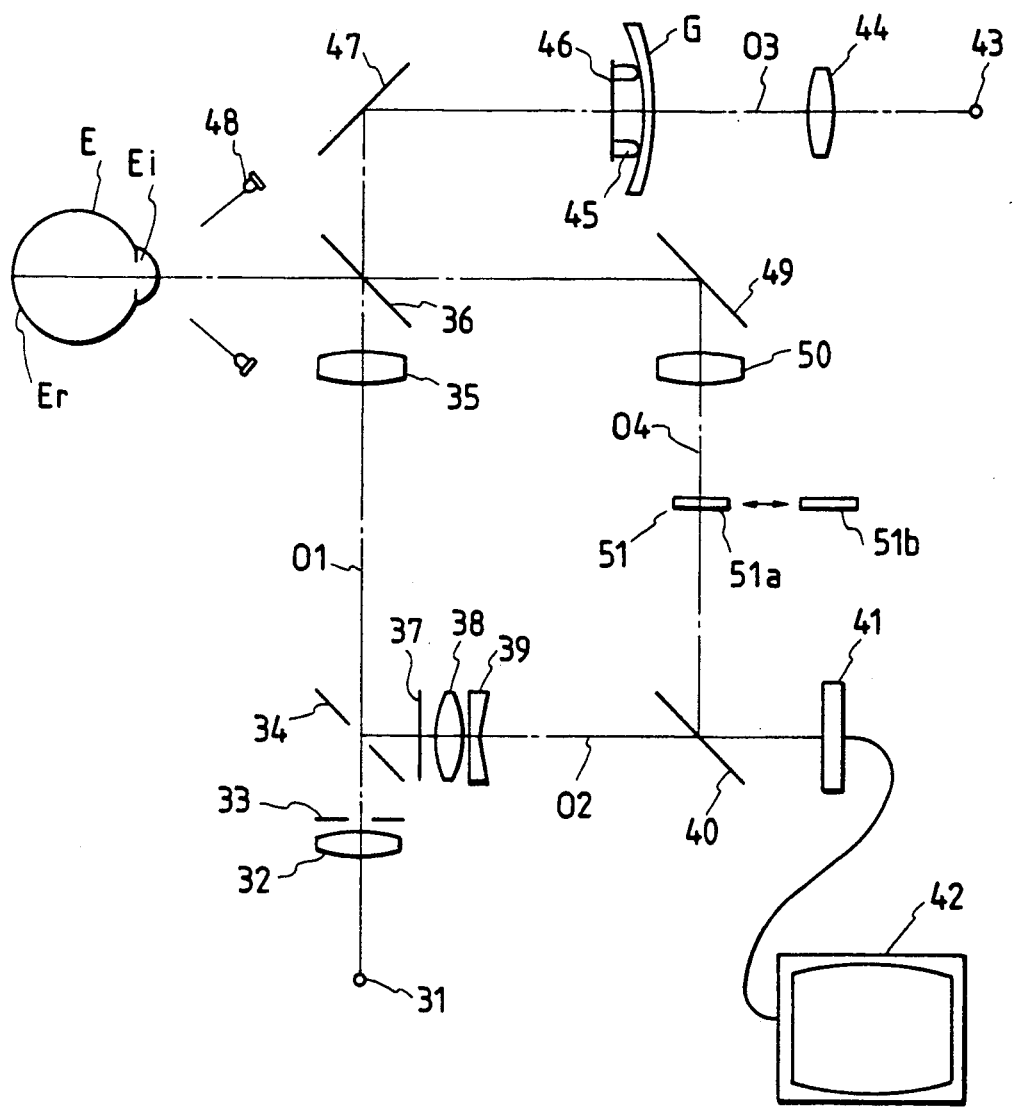
FIG. 10 is a schematic view which illustrates a third embodiment of the present invention.
Figure 11:
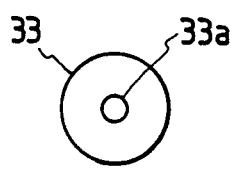
FIG. 11 is a front elevational view which illustrates a projecting diaphragm.
Figure 12:
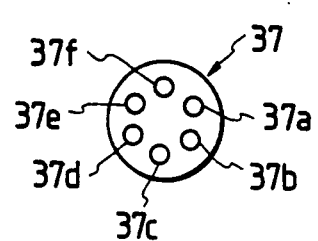
FIG. 12 is a front elevational view which illustrates a measuring diaphragm.
Figure 13:
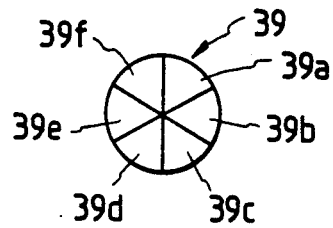
FIG. 13 is a front elevational view which illustrates a separation prism.

FIG. 10 is a structural view which illustrates a third embodiment of the present invention. Referring to FIG. 10, an eye measuring light source 31, which as well as serves as an index for the measurement, is disposed for the purpose of measuring the refractive power of the eye E to be examined. On the optical path 01 established from the measuring light source 31 to the eye E to be examined, there are successively disposed a lens 32, a projecting diaphragm 33 having an aperture 33a as shown in FIG. 11, a mirror 34 having an aperture, a lens 35 and a dichroic mirror 36. On the optical path 02 in a direction into which the mirror 34 having an aperture reflects light, there are disposed a measuring diaphragm 37 having six apertures 37a to 37f as shown in FIG. 12, a lens 38, a separation prism 39 composed of six wedge prisms 39a to 39f as shown in FIG. 13, a dichroic mirror 40 and an imaging element 41. The output from the imaging element 41 is connected to a TV monitor 42. The light source 31 for measuring the eye E to be examined is disposed in substantially conjugation with the eye fundus Er of the eye E to be examined, the projecting diaphragm 33 and the measuring diaphragm 37 are disposed in conjugation with the pupil Ei and the mirror 34 having an aperture is disposed in substantially conjugation with the pupil Ei.

In order to measure the refractive power of the lens G to be examined and to be fitted to the eye E to be examined, a lens measuring light source 43, which is arranged to as well as serve as a measuring index, is disposed. On the optical path 03 established from the lens measuring light source 43 to the dichroic mirror 36, there are disposed a lens 44, a holding member 45 for holding the lens G to be examined, a measuring diaphragm 46 having six aperture similarly to the measuring diaphragm 37 and a reflecting mirror 47.

In order to observe the anterior eye portion of the eye E to be examined, one or more illuminating light sources 48 are disposed to confront the eye E to be examined. On the optical path 04 established in a direction along which light passes from the eye E to the dichroic mirror 36, a reflecting mirror 49 is disposed. In a direction into which light is reflected by the reflecting mirror 49, a lens 50 and a filter 51 are disposed.

Figure 14A:
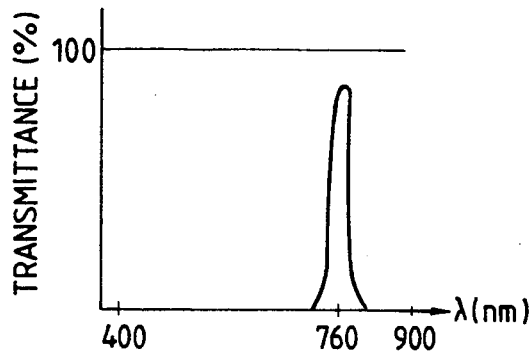
FIGS. 14A and 14B are graphs of the transmittance characteristics of filters.
Figure 14B:
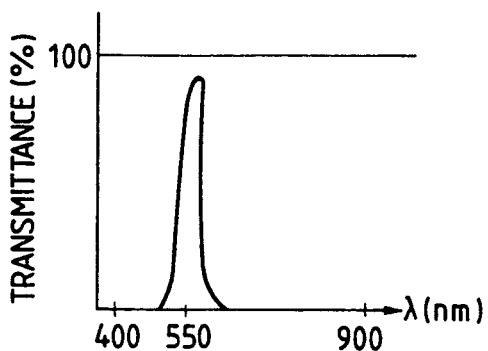

The lens measuring light source 43 emits a visible ray having wavelength of which is about 550 nm, while the illuminating light source 48 emits an infrared ray having wavelength of which is about 760 nm. As described above, the wavelengths of the beams emitted from the two light sources 43 and 48 are separated from each other. A filter 51 is composed of a filter 51a having a transmission characteristic as shown in FIG. 14A (that is, only light emitted from the illuminating light source 48 is transmitted) and a filter 51b having a transmission characteristic as shown in FIG. 14B (that is, only light emitted from the measuring light source 43 is transmitted). A driving means (omitted from illustration) acts to selectively place the filter 51a or the filter 51b to the optical path.

The dichroic mirror 36 has spectrum characteristics with which it transmits the infrared rays emitted from the illuminating light source 48 and reflects the beam emitted from the lens measuring light source 43. The dichroic mirror 40 has spectrum characteristics with which it transmits the beam emitted from the light source 31 for measuring the eye E to be examined and reflects the beams respectively emitted from the lens measuring light source 43 and the illuminating light source 48.

Figure 15:
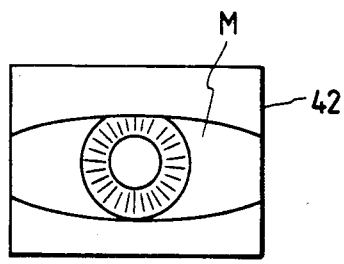
FIGS. 15 and 17 are front elevational views of a TV monitor.

When the refractive power of the eye E to be examined is measured, the illuminating light source 48 is first turned on in a state that the filter 51a has been placed on the optical path 04, so that the anterior eye portion of the eye E to be examined is irradiated with the beam emitted from the illuminating light source 48. The beam reflected by the anterior eye portion passes through the dichroic mirror 36 before it travels along the optical path 04. Then, it is reflected by the reflecting mirror 49 before it passes through the lens 50 and the filter 51a. Then, it is reflected by the dichroic mirror 40 before it is imaged as the image M of the anterior eye portion on the imaging element 41, the thus formed image M of the anterior eye portion being then displayed on a TV monitor as shown in FIG. 15.

Figure 16:
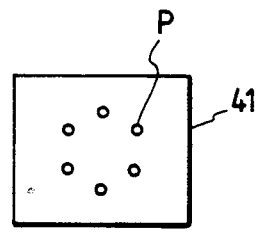
FIG. 16 is a front elevational view which illustrates an imaging element.

An examiner subsequently performs the alignment operation while observing the above-described image M of the anterior eye portion. Then, the illuminating light source 48 is turned off after the alignment has been ended. Subsequently, the light source 31 for measuring the eye E to be examined is turned on. The beam emitted from the measuring light source 31 travels along the optical path 01 in such a manner that it passes through the lens 32, the projecting diaphragm 33, the aperture portion of the mirror 34 having an aperture and the lens 35 before it is reflected by the dichroic mirror 36. Thus, it reaches to the eye E to be examined. The beam reflected from the eye fundus Er returns along the same optical path before it is reflected by the mirror 34 having an aperture. Then, it travels along the optical path 02 in such a manner that it passes through the measuring diaphragm 37 and the lens 38 before it is separated from the optical axis by the separation prism 39. Subsequently, it is projected on the surface of the imaging element 41 via the dichroic mirror 40 as six reflected beam images P as shown in FIG. 16. The refractive power of the eye E to be examined can be calculated from the positional relationship between the reflected beam images P.

When the lens G to be examined is measured, only the lens measuring light source 43 is turned on in a state that the lens G to be examined has been brought into contact with the holding member 45 so as to be fixed on the optical path 03 and as well as the filter 51b has been inserted into the optical path 04. The beam emitted from the lens measuring light source 43 is made to be a collimated beam by the lens 44. The collimated beam is then incident upon the lens G to be examined. Then, it is reflected by the reflecting mirror 47, the dichroic mirror 36, and the reflecting mirror 49 via the measuring diaphragm 46. Subsequently, it passes through the lens 50 and the filter 51b before it is reflected by the dichroic mirror 40. As a result, it is projected on the imaging element 41 as the six transmitted beam images similarly to those shown in FIG. 16. Therefore, the refractive power and the effect of the prism of the lens G to be examined can be calculated from the positional relationship between the transmitted beam images.

The filter 51a is inserted into the optical path 04 when the anterior eye portion is observed. Therefore, the beam from, for example, the room light can be shielded by the filter 51a so that the image M of the anterior eye portion can be clearly displayed on the TV monitor 42. When the refractive power of the lens G to be examined is measured, the filter 51b is inserted. Therefore, the beam from, for example, the room light is shielded by the filter 51b so that the transmitted beam images can be cleared and the refractive power can thereby be measured accurately.

Figure 17:
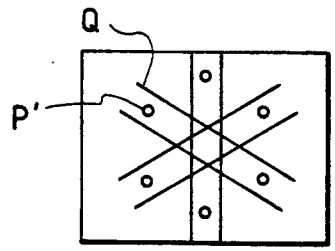

The alignment operation for aligning the optical axis of the lens G to be examined with the optical path 03 can be performed by utilizing the positions of the transmitted beam images of the lens G to be examined. For example, it can be easily performed in such a manner that a radial mark Q as shown in FIG. 17 is electrically generated on the TV monitor 42 and a transmitted beam image P' from the lens G to be examined is output to the TV monitor 42 so as to align the center of the transmitted beam image P' with the center of the mark Q.

Although the filter 51 is disposed between the lens 50 and the dichroic mirror 40 according to the above-described embodiment, another structure may be empoloyed which is arranged in such a manner that the filters 51a and 51b are selectively inserted into the individual positions in the optical path 04 established from the dichroic mirror 36 to the dichroic mirror 40. The beam emitted from the lens measuring light source 43 or the illuminating light source 48 is not limited to the above-described wavelength. Any beam included in the infrared ray region or the visible ray region may be employed if they can be separated. In this state, the filter 51a or 51b, which corresponds to the selected beam, may be used.

Figure 18:
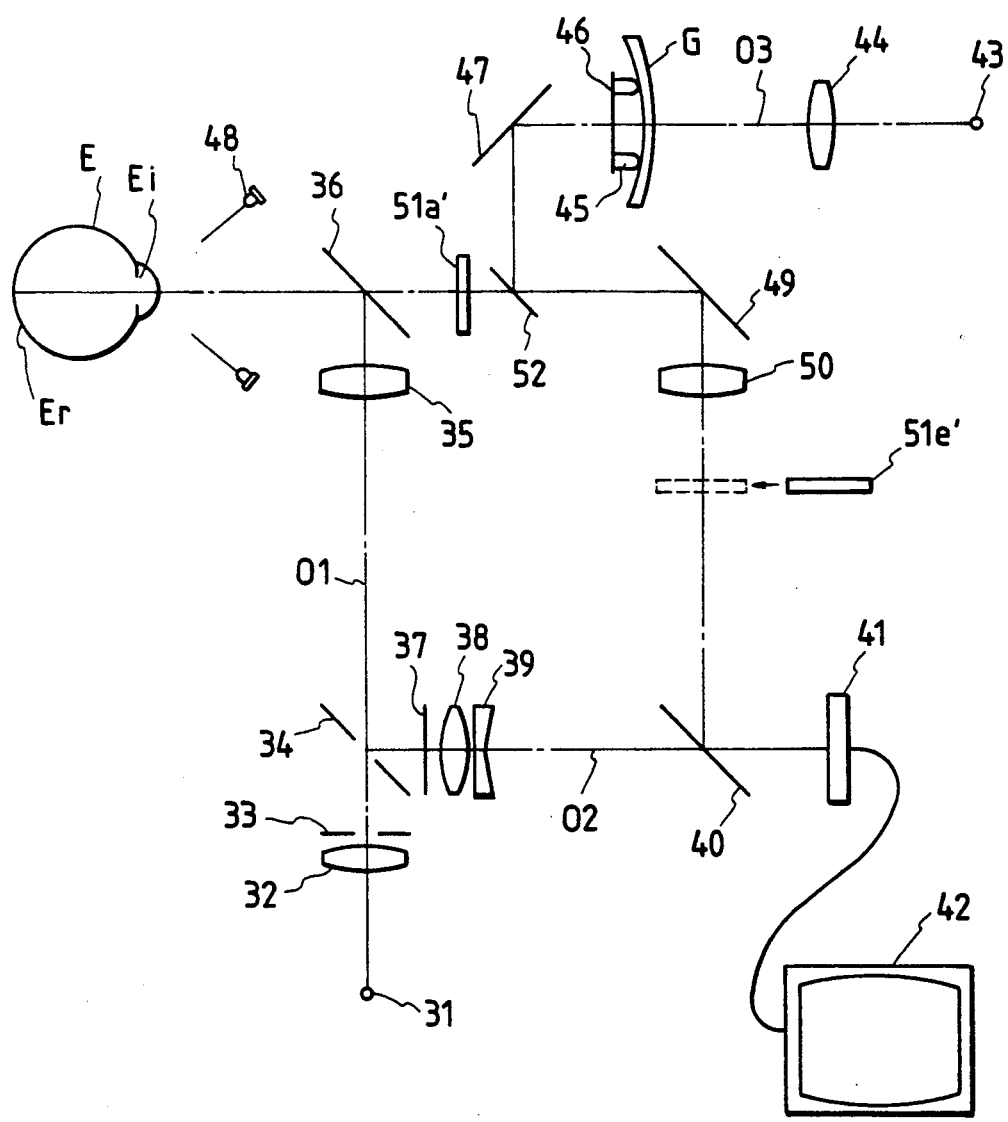
FIG. 18 is a schematic view which illustrates a fourth embodiment of the present invention.

FIG. 18 is a structural view which illustrates a fourth embodiment of the present invention. Referring to FIG. 18, the optical system for measuring the refractive power of the eye E to be examined and the optical system for observing the anterior eye portion are similarly arranged to those according to the embodiment shown in FIG. 10. However, in a direction into which a beam is reflected by the reflecting mirror 47, a dichroic mirror 52 is disposed and a filter 51a' is disposed between the dichroic mirrors 52 and 36. A filter 51b' is detachably disposed between the lens 50 and the dichroic mirror 40. The dichroic mirror 52 has spectrum characteristics with which it transmits the beam emitted from the illuminating light source 48 and reflects the beam emitted from the lens measuring light source 43. The transmission characteristic of the filter 51a' or the filter 51e' is arranged to be the same as that of the filter 51a or the filter 51b shown in FIG. 10.

When the anterior eye portion of the eye E to be examined is observed, the filter 51e' is retracted from the optical path so as to radiate the beam emitted from the illuminating light source 48 to the anterior eye portion of the eye E to be examined. The beam reflected by the anterior eye portion passes through the dichroic mirror 36, the filter 51a' and the dichroic mirror 52 before it is reflected by the reflecting mirror 49. Then, it is reflected by the dichroic mirror 40 via the lens 50 before it is projected to the surface of the imaging element 41'. As a result, the image M of the anterior eye portion is displayed on the TV monitor 42.

When the refractive power of the lens G to be examined is measured, the lens measuring light source 43 is turned on in a state that the filter 51e' has been placed on the optical path and the lens G to be examined has been brought into contact with the holding member 45. The beam emitted from the measuring light source 43 travels along the optical path 03 and passes through the lens 44, the lens G to be examined and the measuring diaphragm 46. Then, it is reflected by the reflecting mirror 47, the dichroic mirror 52, and the reflecting mirror 49 before it passes through the lens 50 and the filter 51e'. Then, it is reflected by the dichroic mirror 40 before the transmitted beam images are formed on the imaging element 41. As a result, the refractive power can be calculated from the positions of the transmitted beam images. The effects of the filters 51a' and 51e' are the same as those according to the above-described embodiments.

As described above, the ophthalmological measuring apparatus according to this embodiment is arranged in such a manner that the optical position detecting sensor is used to observe the anterior eye portion and as well as to measure the refractive power of the eye to be examined and the lens to be examined. Furthermore, the wavelength of the beam for observing the anterior eye portion and that of the beam for measuring the refractive power of the lens to be examined are separated from each other. When the anterior eye portion is observed, the optical member, which transmits only a predetermined wavelength region including the wavelength of the beam for observing the anterior eye portion, is inserted into the optical system for observing the anterior eye portion. When the refractive power of the lens to be examined is measured, the optical member, which transmits only a predetermined wavelength region including the wavelength of the beam for measuring the lens to be examined, is inserted into the optical system for measuring the refractive power of the lens to be examined. Therefore, the refractive power of the eye to be examined and that of the lens to be examined can be accurately measured while reducing the cost of the overall apparatus and simplifying the overall structure.

Figure 19:
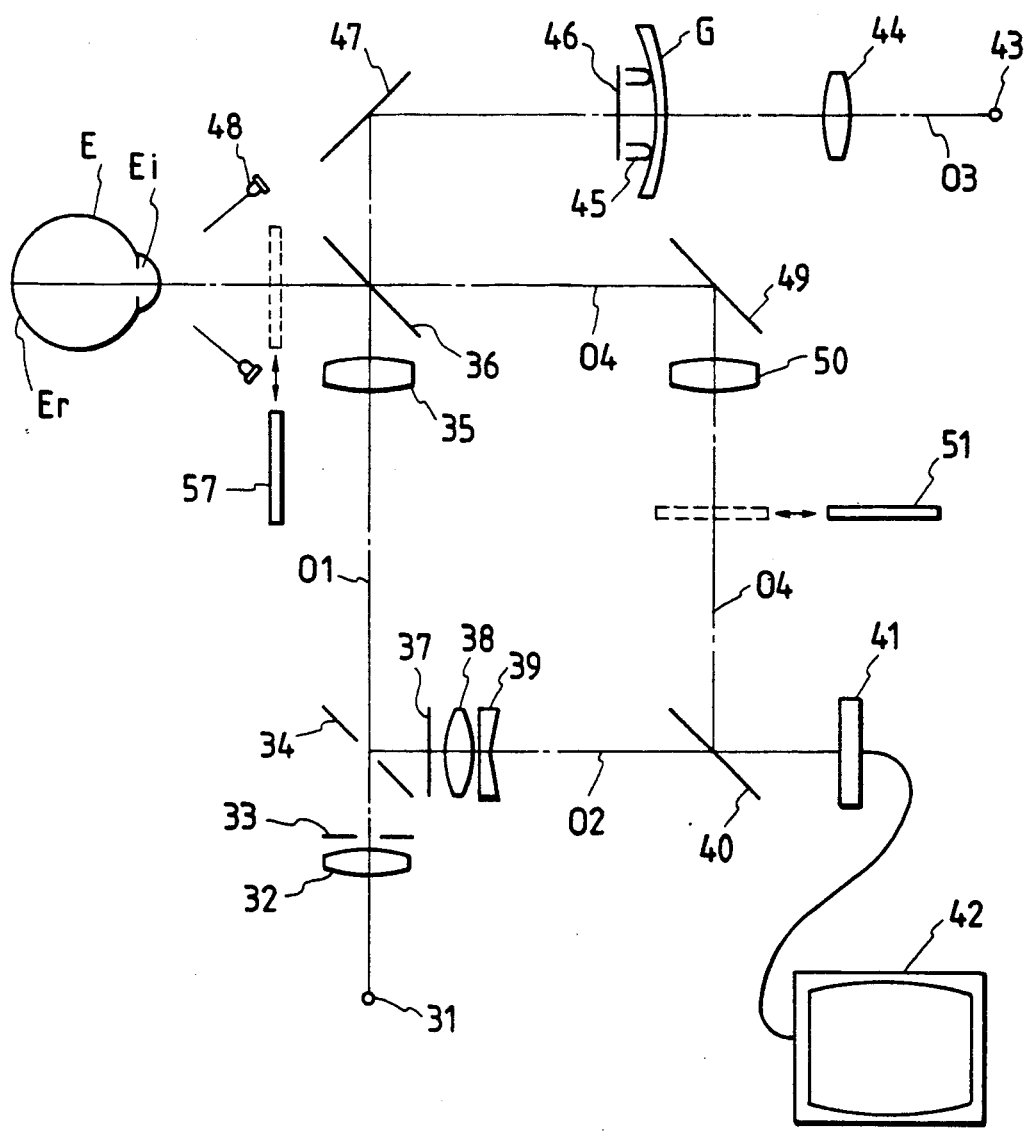
FIG. 19 is a schematic view which illustrates a fifth embodiment of the present invention.

FIG. 19 is a structural view which illustrates a fifth embodiment of the present invention, where the same reference numerals as those according to the above-described embodiments represent the same elements.

One or more illuminating light sources 48 for observing the anterior eye of the eye E are disposed to confront the eye E to be examined. On the optical path rectilinearly extending from the eye E to be examined to the dichroic mirror 36, the reflecting mirror 49, the lens 50 and the detachable light insulating plate 51 are disposed.

When the eye E to be examined is observed, the light shielding plate 57 is retracted from the optical path 01 and the light shielding plate 51 is also retracted from the optical path 04. Then, the illuminating light source 48 is turned on so as to radiate light to the anterior eye portion. The beam reflected from the anterior eye portion of the eye E to be examined passes through the dichroic mirror 36 before it is reflected by the reflecting mirror 49. Then, it is reflected by the dichroic mirror 40 via the lens 50. As a result, it is imaged as the image M of the anterior eye portion on the imaging element 41. The image M of the anterior eye portion is, as shown in FIG. 15, displayed on the TV monitor 42. When the refractive power is measured after the alignment has been completed, the light shielding plate 51 is inserted into the optical path 04 in a state that the light shielding plate 57 has been retracted from the optical path 01.

When the refractive power of the lens G to be examined is measured, the lens measuring light source 43 is turned on in a state that the lens G to be examined has been brought into contact with the holding member 45 so as to be fixed, the light shielding plate 57 has been inserted into the optical path 01 and the light shielding plate 51 has been retracted from the optical path 04.

Figure 20:
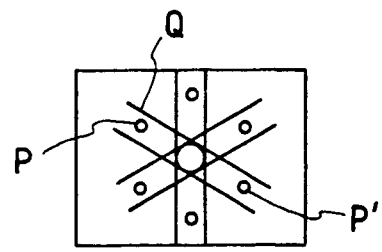
FIG. 20 illustrates reflected beam images on the TV monitor.

The alignment operation to align the optical axis of the lens G to be examined with the optical path 03 can be performed by utilizing the position of the reflected beam P' on the imaging element 41. For example, the lens G to be examined can be aligned in such a manner that a radial mark Q as shown in FIG. 20 is electrically generated on the TV monitor 42. Furthermore, a reflected beam P' is transmitted to the TV monitor 42 so as to align the center of the transmitted beam P' with the center of the mark Q.

The reason why the light shielding plate 57 is used at this measurement operation is that the refractive power must be accurately measured by preventing the fact that the beam emitted from, for example, a room light, is received by the imaging element 41 after it has been reflected by, for example, the face of an examiner.

Figure 21:
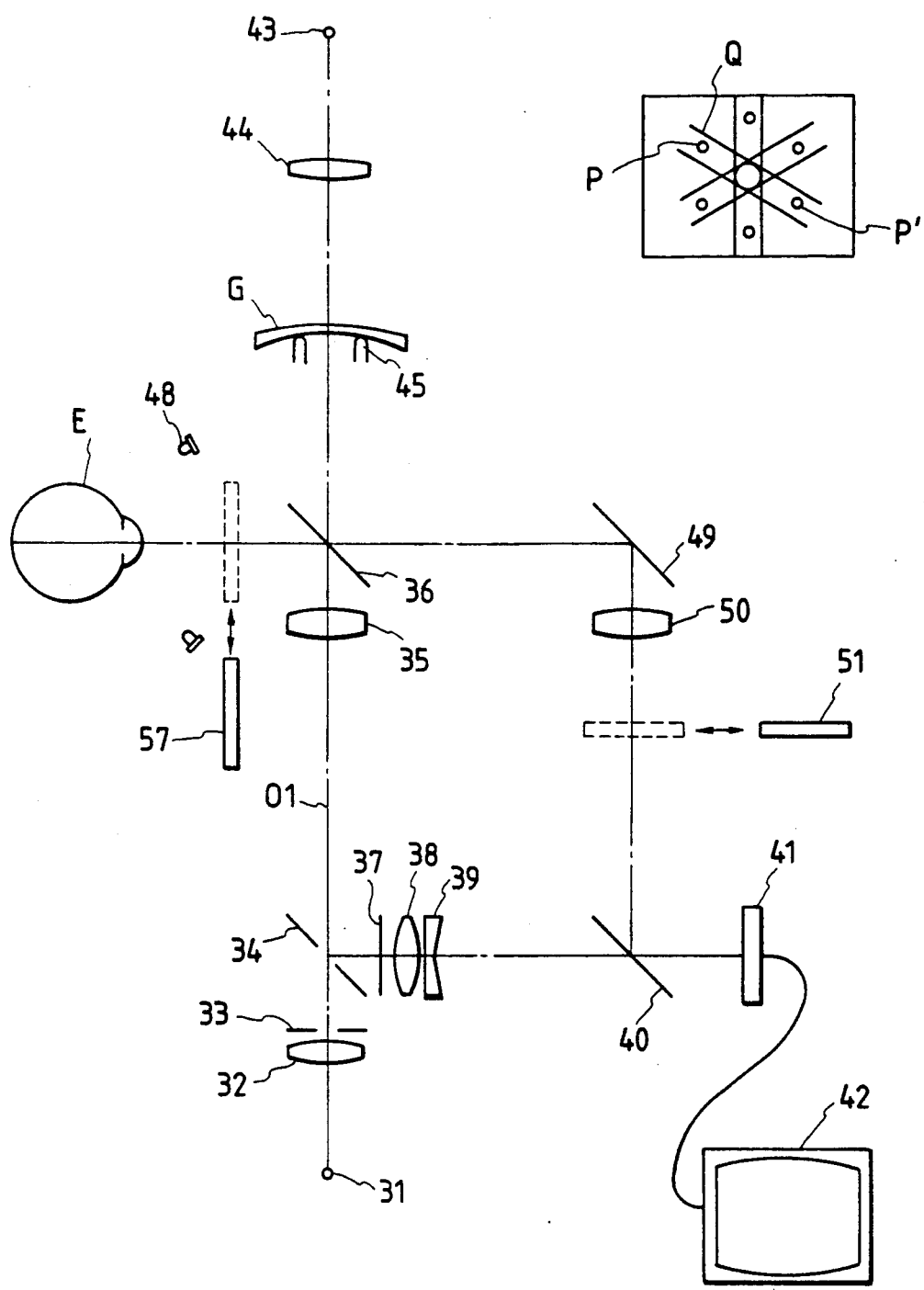
FIGS. 21, 22, 23 and 24 are respectively schematic views which illustrate a sixth, seventh, eighth and ninth embodiments of the present invention.

According to a sixth embodiment shown in FIG. 21, the diaphragm 46 and the reflecting mirror 47 are omitted from the elements disposed on the optical path 03 shown in FIG. 19. In this state, the beam travels along the optical axis 01 so as to pass through the diaphragm 37.

Figure 22:
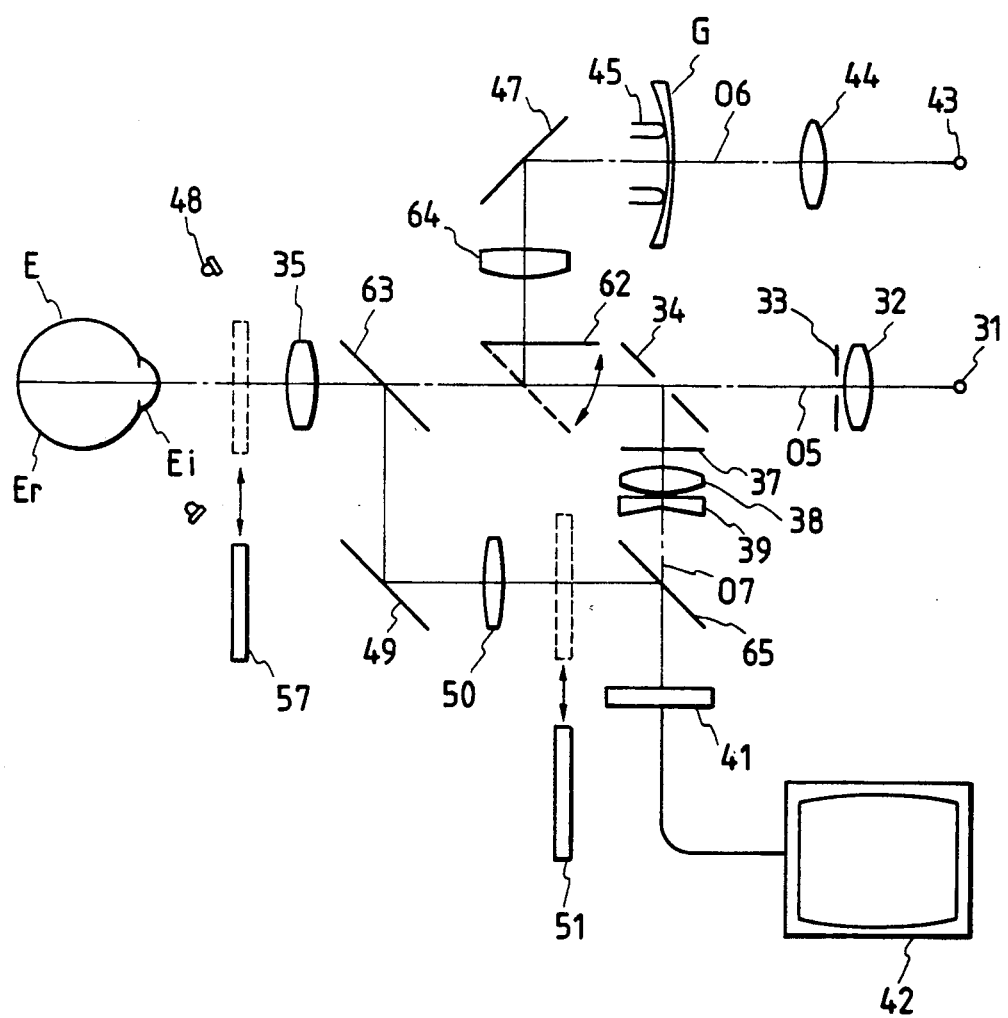

FIG. 22 is a structural view which illustrates a seventh embodiment of the present invention. Referring to FIG. 22, a detachable reflecting mirror 62, a dichroic mirror 63 and a light shielding plate 57, which can be inserted/retracted from the optical path 05, are disposed on the optical path 05 extending from the light source 31 for measuring the eye E to be examined to the eye E. In a direction into which a beam is reflected at the dichroic mirror 63, the reflecting mirror 49 is disposed, while the lens 50, the light shielding plate 51, which can be inserted/retracted from the optical path and a dichroic mirror 65 are disposed in a direction into which a beam is reflected at the reflecting mirror 49. The reflecting mirror 62 is inserted into the optical path 05 or retracted from the same when it is used.

When the refractive power of the eye E to be examined is measured, the reflecting mirror 62 is retracted from the optical path 05 and the illuminating light source 48 for use to observe the anterior eye portion is turned on so that the anterior eye portion is irradiated with light. The beam reflected from the anterior eye portion is reflected by the dichroic mirror 63 and the reflecting mirror 49. Furthermore, it is reflected by the dichroic mirror 65 via the lens 50 so that it is projected to the surface of the imaging element 41 as the image M of the anterior eye portion. The thus formed image M of the anterior eye portion is transmitted to the TV monitor 42. The display formed on the TV monitor 42 is observed by an examiner to perform the alignment.

After the alignment operation has been completed, the illuminating light source 48 is turned off and the light source 31 for measuring the eye E to be examined is turned on. The light insulating plates 51 and 57 act as those according to the embodiment shown in FIG. 21.

Figure 23:
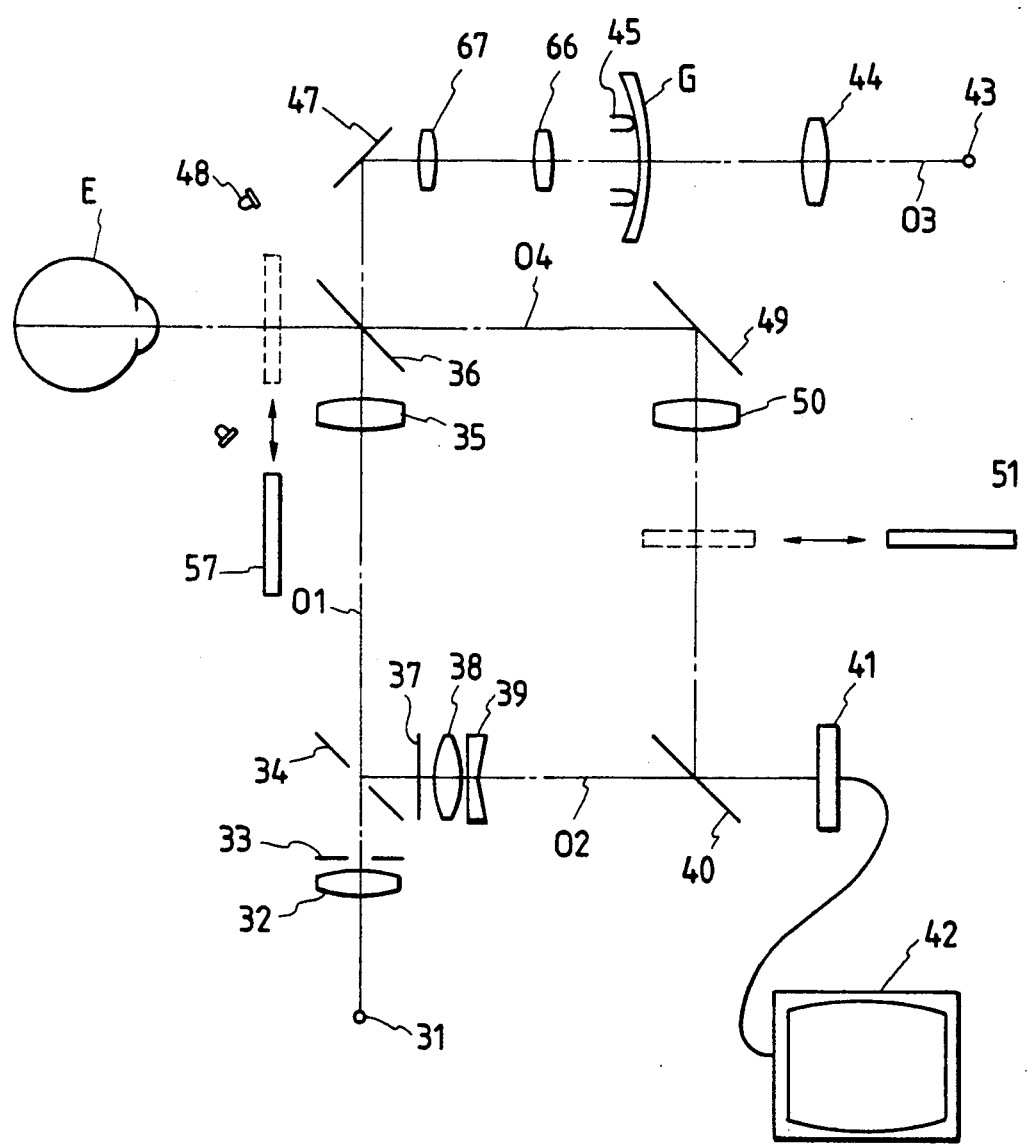

FIG. 23 is a structural view which illustrates an eighth embodiment of the present invention. Referring to FIG. 23, two relay lenses 66 and 67 are disposed between the holding member 45 and the reflecting mirror 47 disposed on the optical path 03. The other structure is the same as that according to the above-described embodiments. The lens G to be examined can be positioned suitably for the operation by properly determining the focal distance of each of the relay lenses 66 and 67.

Figure 24:
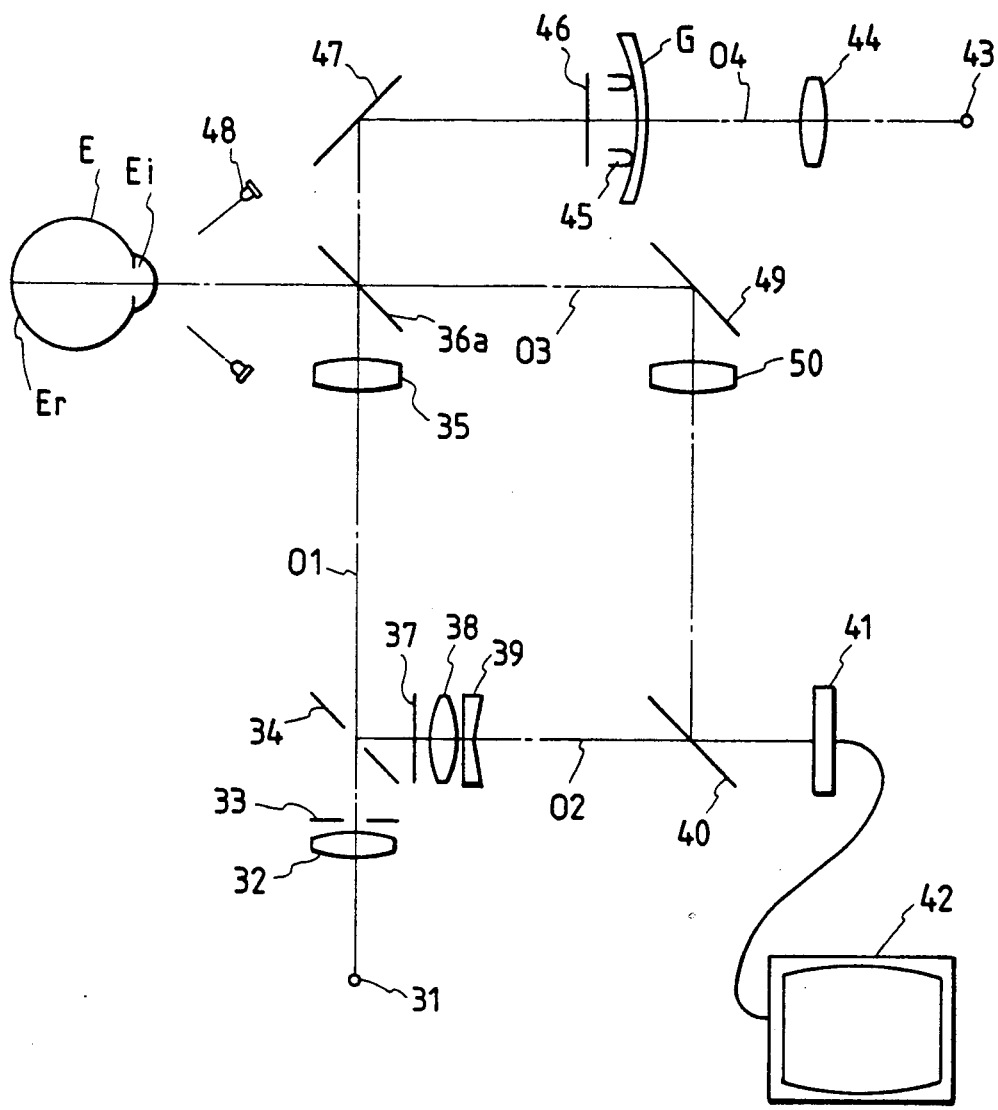

FIG. 24 is a structural view which illustrates a ninth embodiment of the present invention. The optical system for measuring the refractive power of the eye E to be examined and the optical system for observing the anterior eye portion are similarly arranged to those according to the above-described embodiments.

Figure 25:
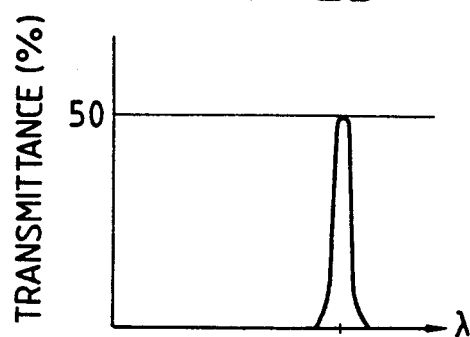
FIG. 25 illustrates the transmittance characteristics of the filter.

The ninth embodiment is arranged in such a manner that the dichroic mirror 36a has a characteristic as shown in FIG. 25, with which only the wavelength of the beam emitted from the illuminating light source 48, as shown in FIG. 25, is transmitted by a quantity of about 50%.

The wavelength of the beam emitted from the light source 43 for measuring the refractive power of the lens G to be examined is the same as that emitted from the light source 48. The beam emitted from the above-described light source 43 is reflected by the dichroic mirror 36a before it passes through the mirror 49, the lens 50 and the dichroic mirror 40. As a result, it reaches to the imaging element.

According to this embodiment, the dichroic mirror 36a considerably reduces disturbance light which passes through the optical path 03 and made incident upon the imaging element 41.

Although the influence of the disturbance light is eliminated by using the dichroic mirror 36a according to this embodiment, the transmittance may, of course, be set to a value other than 50% if the influence of the disturbance or the like can be eliminated.

Although the invention has been described in its preferred form with a certain degree of particularly, it is understood that the present disclosure of the preferred form has been changed in the details of construction and the combination and arrangement of parts may be resorted to without departing from the spirit and the scope of the invention as hereinafter claimed.

We claim:

1. An ophthalmological apparatus comprising:
   an alignment observing system having a first light sensor which is substantially conjugate with an anterior eye portion of an eye to be examined;
   an eye refractive power measuring system having a first light source for projecting a beam to an eye fundus of the eye to be examined and arranged to measure a refractive power of the eye by receiving light reflected at the eye fundus by means of a second light sensor;
   means for holding a lens to be examined at a position which is different from a position where the eye to be examined is placed; and
   a lens refractive power measuring system having a second light source for projecting a beam to a lens to be examined and arranged to measure a lens refractive power by receiving the beam from said second light source which passes through said lens, by means of a third light sensor,
   wherein said first light source and said second light source are different from each other and said third light sensor is commonly used with at least either said first light sensor or said second light sensor.

2. An ophthalmological apparatus according to claim 1, wherein said third light sensor is non-conjugate with a position at which said lens to be examined is placed.

3. An ophthalmological apparatus according to claim 1, wherein said first, second and third light sensors are composed of a light sensor which is commonly used.

4. An ophthalmological apparatus according to claim 1, further comprising a display monitor which is connected to said commonly used third light sensor, said display monitor having a positioning mark formed on a predetermined portion thereof.

5. An ophthalmological apparatus according to claim 1, wherein said alignment observing system has a light source for illuminating the anterior eye portion.

6. An ophthalmological apparatus according to claim 1, wherein said lens refractive power measuring system has a relay optical system between said third light sensor and said means for holding said lens to be examined.

7. An ophthalmological apparatus according to claim 5, wherein at least a portion of an optical path for said lens refractive power measuring system is commonly used by said alignment observing system.

8. An ophthalmological apparatus according to claim 7 further comprising light selection means for selectively transmitting only light emitted from said light source for illuminating the anterior eye portion and light emitted from said second light source.

9. An ophthalmological apparatus according to claim 8, wherein said light selection means is a wavelength selection filter.

10. An ophthalmological apparatus according to claim 8, wherein said light selection means is a light shielding plate which can be freely inserted/retracted into/from a optical path.

11. An ophthalmological apparatus according to claim 1, wherein said alignment observing system has a display monitor which is commonly used to observe an alignment of said eye refractive power measuring system and to observe an alignment of said lens refractive power measuring system.

12. An ophthalmological apparatus according to claim 5, further comprising wavelength selection means for connecting an optical path for said lens refractive power measuring system to an optical path of said alignment observing system, permitting a wavelength of light emitted from said second light source to be the same as that of light emitted from said light source for illuminating the anterior eye portion, and transmitting only light of said wavelength along the optical path of said alignment observing system.

* * * * *

UNITED STATES PATENT AND TRADEMARK OFFICE
CERTIFICATE OF CORRECTION

PATENT NO. : 5,144,346

DATED : September 1, 1992

INVENTOR(S) : YUKITSUGU NAKAMURA, ET AL.

It is certified that error appears in the above-identified patent and that said Letters Patent is hereby corrected as shown below:

[54] TITLE

Line 1, "OPHTHALOMOLOGICAL" should read --OPHTHALMOLOGICAL--.

COLUMN 1

Line 2, "OPHTHALOMOLOGICAL" should read --OPHTHALMOLOGICAL-.
    Line 7, "ophthalomologi-" should read --ophthalmologi---.
    Line 48, "advangates" should read --advantages--.

COLUMN 2

Line 31, "an" should read --a--.
    Line 46, "made" should read --made to--.
    Line 65, "though" should read --through--.

UNITED STATES PATENT AND TRADEMARK OFFICE
CERTIFICATE OF CORRECTION

PATENT NO. : 5,144,346
DATED : September 1, 1992
INVENTOR(S) : YUKITSUGU NAKAMURA, ET AL.

It is certified that error appears in the above-identified patent and that said Letters Patent is hereby corrected as shown below:

COLUMN 3

Line 36, "power Information" should read --power. Information--.

COLUMN 4

Line 44, "being" should be deleted.

COLUMN 5

Line 51, "hold" should read --held--.

UNITED STATES PATENT AND TRADEMARK OFFICE
CERTIFICATE OF CORRECTION

PATENT NO. : 5,144,346

DATED : September 1, 1992

INVENTOR(S) : YUKITSUGU NAKAMURA, ET AL.

It is certified that error appears in the above-identified patent and that said Letters Patent is hereby corrected as shown below:

COLUMN 6

Line 14, "substantially" should read --substantial--.
Line 18, "substantially" should read --substantial--.
Line 28, "aperture" should read --apertures--.
Line 39, "having" should read --the--.
Line 40, "having" should read --the--.

COLUMN 7

Line 14, "ended." should read --completed.--.

COLUMN 8

Line 18, "51b ," should read --51b,--.
Line 20, "structural" should read --schematic--.
Line 29, "filter 51b'" should read --filter 51e'--.
Line 48, "41'" should read --41--.

UNITED STATES PATENT AND TRADEMARK OFFICE
CERTIFICATE OF CORRECTION

PATENT NO. : 5,144,346
DATED : September 1, 1992
INVENTOR(S) : YUKITSUGU NAKAMURA, ET AL.

It is certified that error appears in the above-identified patent and that said Letters Patent is hereby corrected as shown below:

COLUMN 9

Line 23, "structural" should read --schematic--.

COLUMN 10

Line 13, "structural" should read --schematic--.
Line 17, "from" should read --into/from--.
Line 23, "from" should read --into/from--.
Line 47, "structural" should read --schematic--.
Line 57, "structural" should read --schematic--.

COLUMN 12

Line 24, "7 further" should read --7, further--.
Line 34, "a" should read --an--.

Signed and Sealed this

Ninth Day of November, 1993

Attest:

BRUCE LEHMAN

*Attesting Officer*    *Commissioner of Patents and Trademarks*